United States Patent
Buckley et al.

(10) Patent No.: US 10,610,114 B2
(45) Date of Patent: Apr. 7, 2020

(54) PATIENT MONITORING DEVICES AND SYSTEMS

(71) Applicants: Jill Buckley, La Jolla, CA (US); Jay L. Shils, Somerville, MA (US)

(72) Inventors: Jill Buckley, La Jolla, CA (US); Jay L. Shils, Somerville, MA (US)

(73) Assignee: Jill Buckley, La Jolla, CA (US)

( * ) Notice: Subject to any disclaimer, the term of this patent is extended or adjusted under 35 U.S.C. 154(b) by 511 days.

(21) Appl. No.: 15/147,767

(22) Filed: May 5, 2016

(65) Prior Publication Data

US 2016/0354001 A1 Dec. 8, 2016

Related U.S. Application Data

(62) Division of application No. 13/887,660, filed on May 6, 2013, now Pat. No. 9,332,918.

(60) Provisional application No. 61/643,490, filed on May 7, 2012.

(51) Int. Cl.
*A61B 5/04* (2006.01)
*A61B 5/00* (2006.01)
*A61N 1/04* (2006.01)

(52) U.S. Cl.
CPC ........ *A61B 5/04001* (2013.01); *A61B 5/4821* (2013.01); *A61B 5/6824* (2013.01); *A61B 5/6831* (2013.01); *A61B 5/746* (2013.01); *A61B 5/7425* (2013.01); *A61B 5/4029* (2013.01); *A61B 5/4041* (2013.01); *A61B 5/459* (2013.01); *A61B 2560/0475* (2013.01); *A61B 2562/043* (2013.01); *A61B 2562/046* (2013.01); *A61B 2562/14* (2013.01); *A61B 2562/164* (2013.01); *A61B 2562/222* (2013.01); *A61N 1/0456* (2013.01); *A61N 1/0484* (2013.01)

(58) Field of Classification Search
CPC . A61B 5/04001; A61B 5/4821; A61B 5/6824; A61B 5/6831; A61B 5/4029; A61B 5/4041; A61B 5/459; A61B 2562/0209; A61B 2562/043; A61B 2562/046; A61B 2562/14; A61B 2562/164; A61B 2562/221; A61B 2562/222; A61N 1/0456; A61N 1/0484
See application file for complete search history.

(56) References Cited

U.S. PATENT DOCUMENTS

| | | | |
|---|---|---|---|
| 6,341,237 B1 | 1/2002 | Hurtado | |
| 8,731,654 B2 | 5/2014 | Johnson et al. | |
| 2002/0095080 A1* | 7/2002 | Cory | A61B 5/04001 600/393 |

(Continued)

*Primary Examiner* — Devin B Henson
(74) *Attorney, Agent, or Firm* — Knobbe, Martens, Olson & Bear, LLP

(57) ABSTRACT

In one embodiment, the invention relates to systems, methods, and apparatus relating to the detection of a neuropathy such as a perioperative neuropathy. In one embodiment, a wristband comprising a plurality of anodes and cathodes is used. The wristband can be a component in a electrode array that includes a plurality of reference or recording electrodes. The electrode array can be configured to stimulate and collect responsive signals from an ulnar, a median, radial and posterior tibial nerve. The simulation and signal collection can be performed on a continuous basis for time periods of interest such as a given perioperative time period using a monitoring device.

6 Claims, 15 Drawing Sheets

(56) References Cited

U.S. PATENT DOCUMENTS

| | | |
|---|---|---|
| 2007/0129771 A1 | 6/2007 | Kurtz et al. |
| 2007/0282217 A1 | 12/2007 | McGinnis et al. |
| 2008/0097564 A1* | 4/2008 | Lathrop ................ A61F 5/0118 607/115 |
| 2010/0312124 A1 | 12/2010 | Johnson et al. |
| 2013/0231725 A1* | 9/2013 | Williams ............. A61N 1/0551 607/116 |

* cited by examiner

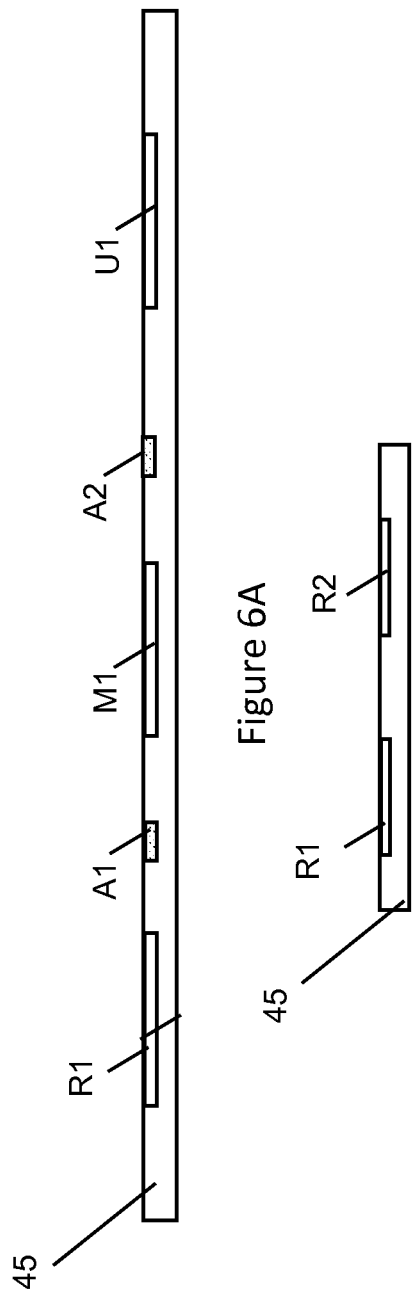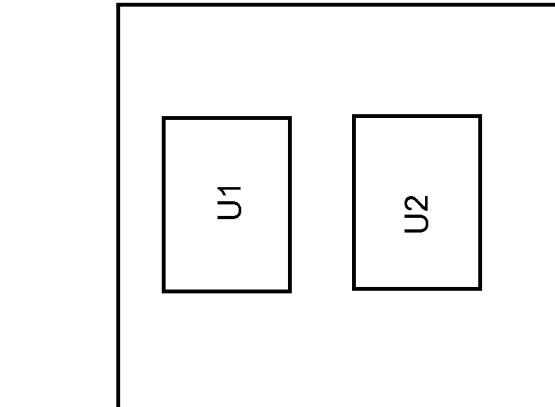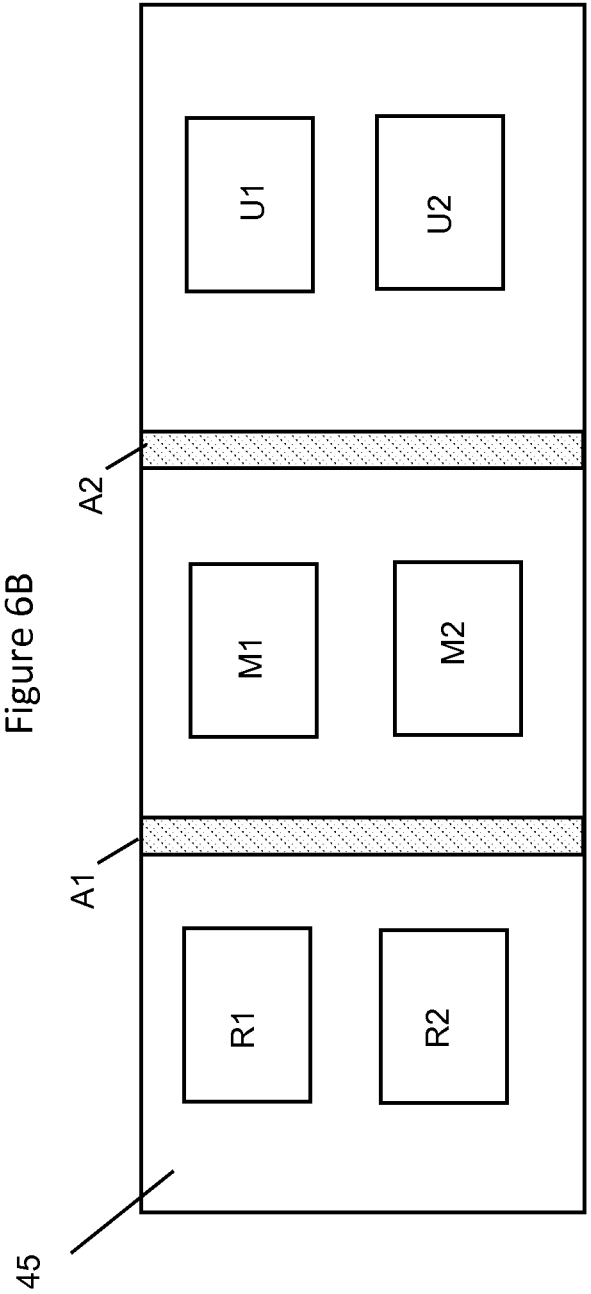

PATIENT MONITORING DEVICES AND SYSTEMS

CROSS-REFERENCE TO RELATED APPLICATIONS

This application is a divisional of U.S. patent application Ser. No. 13/887,660, filed May 6, 2013, now U.S. Pat. No. 9,332,918, which claims priority to U.S. Provisional Patent Application Ser. No. 61/643,490 filed May 7, 2012, the entire disclosure of each of which is incorporated by reference herein.

FIELD OF THE INVENTION

The invention relates generally to the field of patient monitoring and safety. In part, it specifically relates to the monitoring of somatosensory electrical potentials to identify one or more patient states or neuropathies.

SUMMARY OF THE INVENTION

In part, the invention relates to a nerve monitoring system. In one embodiment, the invention includes a non-invasive hand-held monitoring system that tests the integrity of the central and peripheral nervous system. This automated test uses electrodes to generate input signals and receive responsive output signals. These signals can be processed to detect and prevent intraoperative positioning related neuropathies. In one embodiment, the invention relates to an electrode array that includes a first and a second wrist electrode such that each is configured to simultaneously and/or sequentially stimulate three nerves.

Preventing perioperative neuropathy in the peripheral nervous system has many challenges. One challenge arises from the multiple, variably cross-linked tracts of the peripheral nervous system. Nerve injury from perioperative positioning can occur anywhere along the tracts of the peripheral nervous system. Testing the integrity of an ascending tract that is being stimulated can miss branches of the brachial plexus. Monitoring several nerves can address this issue. In addition, by using a wristband-based electrode suitable nerves can be monitored with sufficient accuracy and quickly deployed for monitoring without having the electrode placer undergoing extensive training relating to electrode placement.

In one embodiment, the invention relates to a monitoring system configured for widespread peripheral/dermatomal evoked potential monitoring. Monitoring such potential signals increases detection of upper extremity neural dysfunction. This increase occurs by effectively stimulating and monitoring traffic through the various and unpredictable branches of the brachial plexus. Widespread transdermal stimulation and monitoring can detect more events of interest and thus prevent more peripheral neural dysfunction.

Using widespread peripheral/dermatomal sensory evoked potentials allows operators to monitor and evaluate nerve health and function. Raw evoked potentials, a type of responsive signal generated from stimulated nerves, can be digitized and processed to convey interpretable data and human-readable alerts. These alerts can indicate a neuropathy or other state of interest relating to the nervous system such as limb position and nerve compression.

In part, the invention relates to devices and methods for implementing continuous peripheral nerve monitoring. This monitoring can be performed relative to one or more established baseline values. This comparison of responsive signals from stimulated nerves to a baseline allows detection of various potential neuropathies and changes in patient states such as position states. For example, significant changes in nerve conduction can be identified and triggered upon. A given limb position can compress a region and cause nerve damage if unresolved in time. Alerts can then be generated to prompt intervention and thus prevent peripheral neuropathies causing patient discomfort or injury. This monitoring method can be used as a standard of care for all operations and other scenarios that cause neuropathies.

In one embodiment, the invention includes a computer-based system and methods configured for widespread peripheral/dermatomal somatosensory evoked potentials monitoring. In one embodiment, an electrode array can be used along with a monitoring system to evaluate the entire brachioplexus for time periods of interest. As a result, missed operative positioning neuropathies that could be missed can be prevented. Non-invasive monitoring configured to avoid dermal needle placement is another embodiment of the invention. In one embodiment, an electrode array is one aspect of the invention. A suitable electrode array can include a plurality of stimulating electrodes and a plurality of recording or reference electrodes.

In one aspect, the invention relates to a nerve monitoring system. The system can include a wristband. The wristband can include a first pair of electrodes, a second pair of electrodes, a third pair of electrodes, and an elongate flexible substrate, first electrode, second electrode, and third electrode disposed in or on the flexible substrate; and a first electrical lead having an electrode contacting end and a monitoring device contacting end, the electrode contacting end in electrical communication with at least one electrode in the first pair of electrodes.

In one embodiment, the first pair of electrodes is positioned relative to the elongate flexible substrate such that each electrode in the first pair is positionable above a median nerve when the wristband is worn. The second pair of electrodes can be positioned relative to the elongate flexible substrate such that each electrode in the second pair is positionable above a radial nerve when the wristband is worn. The third pair of electrodes can be positioned relative to the elongate flexible substrate such that each electrode in the third pair is positionable above an ulnar nerve when the wristband is worn.

In one embodiment, the flexible substrate has one or more demarcations configured to identify a boundary between one or more nerves or bones disposed relative to nerves. The system can further include a second electrical lead having an electrode contacting end and a monitoring device contacting end, the electrode contacting end in electrical communication with at least one electrode in the second pair of electrodes. The system can further include a third electrical lead having an electrode contacting end and a monitoring device contacting end, the electrode contacting end in electrical communication with at least one electrode in the third pair of electrodes. The system can further include a monitoring device in electrical communication with the monitoring device contacting end of the first electrical lead, the monitoring device configured to stimulate one or more electrodes in the first electrode pair and monitor responsive signals from one or more of a radial, ulnar or median nerve.

In one embodiment, the monitoring device includes a housing, one or more electrode input ports configured to connect to one or more electrical leads, a processor disposed in the housing, a memory storage device configured to store measured baseline signals, a timer configured to synchronize pulse delivery, a pulse generator configured to transmit a plurality of pulses along the first electrical lead, a comparator configured to detect deviations in responsive nerve signals generated following pulse delivery to a nerve, and an alarm generator configured to indicate a change from a first patient state to a second patient state, the memory storage device, the timer, the pulse generator, and the comparator in electrical communication with and responsive to processor control signals. The system can further include an adapter configured to interface with an anesthesia machine such that alerts, nerve signals, or combinations thereof are presented on a display of the anesthesia machine.

In one aspect, the invention relates to processor-based method of detecting a neuropathy in a patient. The method includes noninvasively monitoring a first nerve, a second nerve, and a third nerve, wherein the first nerve, the second nerve, and the third nerve are at least partially disposed in the wrist of the patient; electrically stimulating the first, second, and third nerves; detecting a deviation relative to a baseline signal with respect to a responsive signal generated by one or more of the first, second, and third nerves following the electric stimulation using a processor; comparing the deviation to a predetermined threshold using a processor; and generating an alert indicative of the neuropathy when the deviation exceeds a predetermined threshold. In one embodiment, the neuropathy is a perioperative neuropathy and the alert is displayed on an anesthesia machine. In one embodiment, the first nerve is a radial nerve, wherein the second nerve is a median nerve and wherein the third nerve is an ulnar nerve. The method can further include noninvasively monitoring a fourth nerve at least partially disposed below a knee of the patient. In one embodiment, the fourth nerve is a posterior tibial nerve and wherein the responsive signal is generated by one or more of the first, second, third and fourth nerves.

In one aspect, the invention relates to a nerve monitoring system. The system includes an input port configured to receive a plurality of time varying electrical signals from one or more reference electrodes in a non-invasive electrode array; a comparator in electrical communication with the input port; a processor in electrical communication with the comparator; a display device in electrical communication with the processor; and a memory device storing a plurality of instructions which, when executed by the processor, cause the processor to operate with the display device and the comparator to: control the comparator and cause it to compare one or more of the plurality of time varying electrical signals to one or more baseline signals; determine when a deviation between a baseline signal and one or received signals from the electrode array exceeds an alarm threshold; and control the display device such that an alarm signal is displayed when the alarm threshold has been exceeded.

In one embodiment, the non-invasive electrode array is configured to collect signals from N+M positions on a patient by contacting a skin surface without piercing the same. The electrode array can include a N anode and cathode pairs and M reference electrodes such that each anode and cathode in a pair is positioned to stimulate one or more monitored nerves and each reference electrode is positioned to measure one or more baseline nerves or baseline positions. In one embodiment, N is greater than or equal to six and M is six. In one embodiment, the monitored nerves include a radial nerve of a first hand, an ulnar nerve of the first hand, a median nerve of the first hand, a radial nerve of a second hand, an ulnar nerve of the second hand, and a median nerve of the second hand. In one embodiment, the monitored nerves further include a posterior tibial nerve of a first foot and a posterior tibial nerve of a second foot. In one embodiment, the baseline nerves or baseline positions include FPz, a first Erbs point, a second Erbs point, and a CV.

In one aspect, the invention relates to an electrode array configured to generate and monitored evoked potentials. The electrode array includes a wristband that includes a first pair of electrodes, a second pair of electrodes, a third pair of electrodes, and an elongate first flexible substrate, a second substrate disposed on the first substrate, the first electrode, second electrode, and third electrode disposed in or on the second substrate, wherein one electrode in each pair is an anode and the other electrode in each pair is a cathode, wherein all three anodes are arranged substantially in a first row and wherein all three cathodes are arrange substantially in a second row. In one embodiment, the second substrate is a gel.

In one embodiment, the monitoring device can include a housing, one or more electrode input ports configured to connect to one or more electrical leads, a processor disposed in the housing, a memory storage device configured to store measured baseline signals, a timer configured to synchronize pulse delivery, a pulse generator configured to transmit a plurality of pulses to a the first electrical lead, a comparator configured to detect deviations in responsive nerve signals generated following pulse delivery to a nerve, and an alarm generator configured to indicate a change from a first patient state to a second patient state, a neuropathy or a potential neuropathy.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views. The drawings associated with the disclosure are addressed on an individual basis within the disclosure as they are introduced.

FIGS. 6A-6C are schematic diagrams showing two cross-sectional views and a top view of an exemplary wristband-based electrode according to an illustrative embodiment of the invention.

DETAILED DESCRIPTION

The following description refers to the accompanying drawings that illustrate certain embodiments of the present invention. Other embodiments are possible and modifications may be made to the embodiments without departing from the spirit and scope of the invention. Therefore, the following detailed description is not meant to limit the present invention, rather the scope of the present invention is defined by the claims.

In one embodiment, the invention relates to a non-invasive electrode array that can be used in conjunction with a system or device to monitor peripheral nerve conduction and detect a change in nerve function in response to stimulation signals. These changes in nerve function can be identified based on deviations from predetermined thresholds. Detecting the change can be used to alert an operator to prevent positioning induced neuropathies such as neuropathies from operative positioning. The device or system can be a portable and/or a hand held device configured to connect with the electrode array. Once connected, the device or system can selectively stimulate certain nerves via one or more electrodes and monitor the same. The system or device can also be incorporated in an anesthesia machine or other machine used in a patient diagnosing or treating environment.

Figure 1:
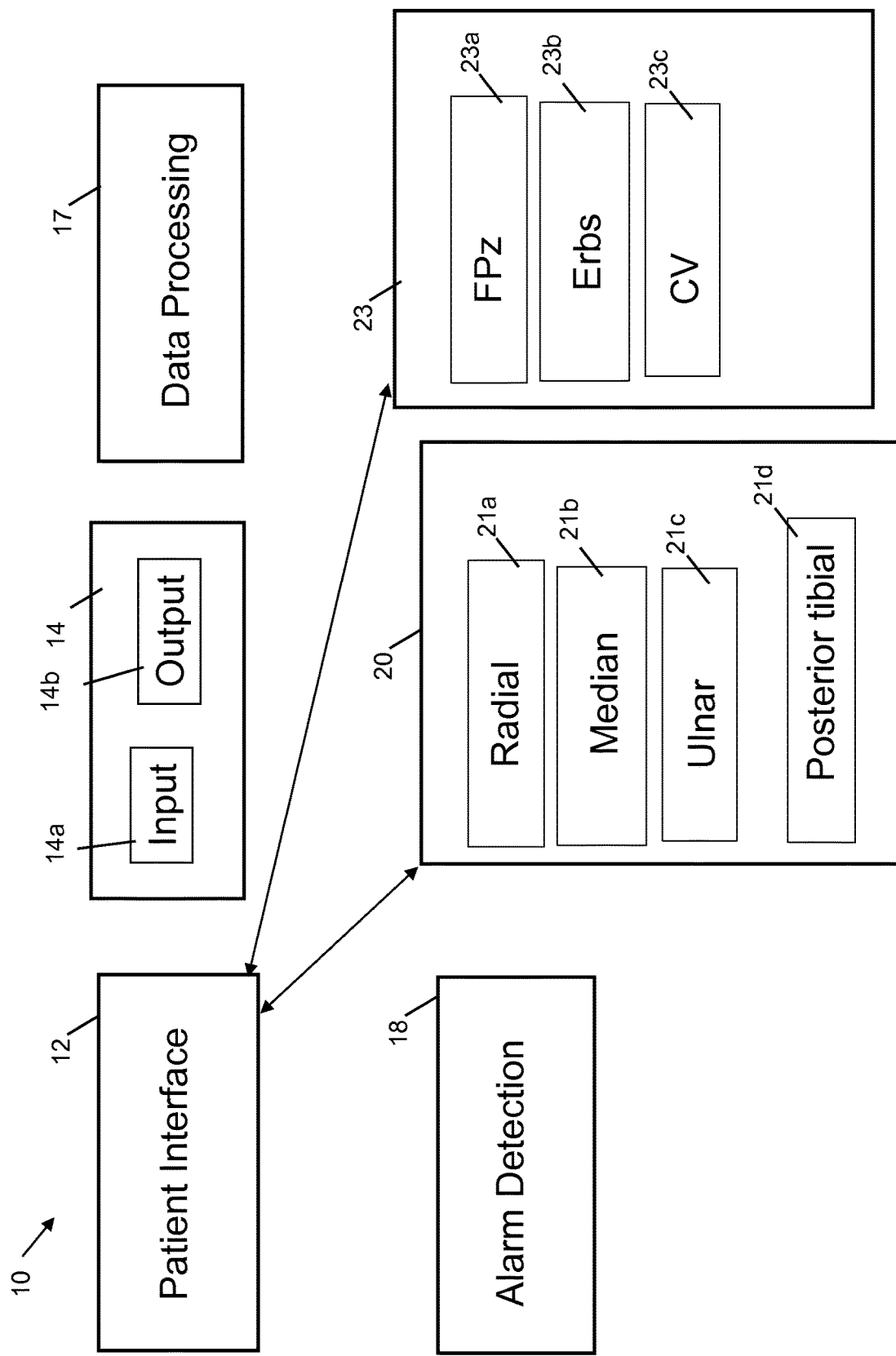
FIG. 1 is a schematic diagram of various components of a nerve monitoring system according to an illustrative embodiment of the invention.

In one embodiment, an exemplary monitoring system includes four subsystems or processing stages. Such an exemplary system is depicted in FIG. 1. The system 10 can include, without limitation, a patient interface subsystem or stage 12; an input/output subsystem or stage 14; a data processing subsystem or stage 17; and an alarm detection subsystem or stage 18. Various other subsystems or processing stages can be used and the individual components of a given monitoring system can be grouped and categorized in different ways. The patient interface can be in electrical communication with an electrode array. The electrode array can include a plurality of stimulation electrodes 20 and a plurality of recording or reference electrodes 23.

The stimulation electrodes 20 are positioned to contact the skin of a patient in order to stimulate a plurality of peripheral nerves. In one embodiment, three peripheral nerves are stimulated. In another embodiment, four peripheral nerves are stimulated. These nerves can include a Radial nerve 21a; a Median nerve 21b; an Ulnar nerve 21c; and a Posterior Tibial nerve 21d. In one embodiment, electrodes are gel type electrodes. These electrodes are configured to stick or adhere to a patient in one embodiment. The recording electrodes 22 can be configured to record relative to FPz 23a, one or both Erb's points 23b, and at CV 23c.

The input subsystem 14a can include an impedance circuit, a pulse generator, an isolator, and energy source. The output subsystem 14b can include an analog to digital converter and an amplifier pre-processor. The data processing system 17 can include an averager, a timer, a filter, a processor, memory storage, and a comparator. In addition, the alarm detection subsystem 18 can include an alarm decision module (software or hardware based) and an output such as a display device or a speaker to announce an alarm. The output system 14b is in electrical communication with the recording electrodes 23 while the input system 14a is in electrical communication with the stimulation electrodes 20.

The monitoring device or system used in a given embodiment can eliminate the need for human analysis. The device or system is automated by software that works with a processor to detect preset thresholds to signal a change from the baseline reading. The software can then alert the anesthesiologist or other operator to reposition an extremity to re-establish the baseline waveform.

Figure 2:
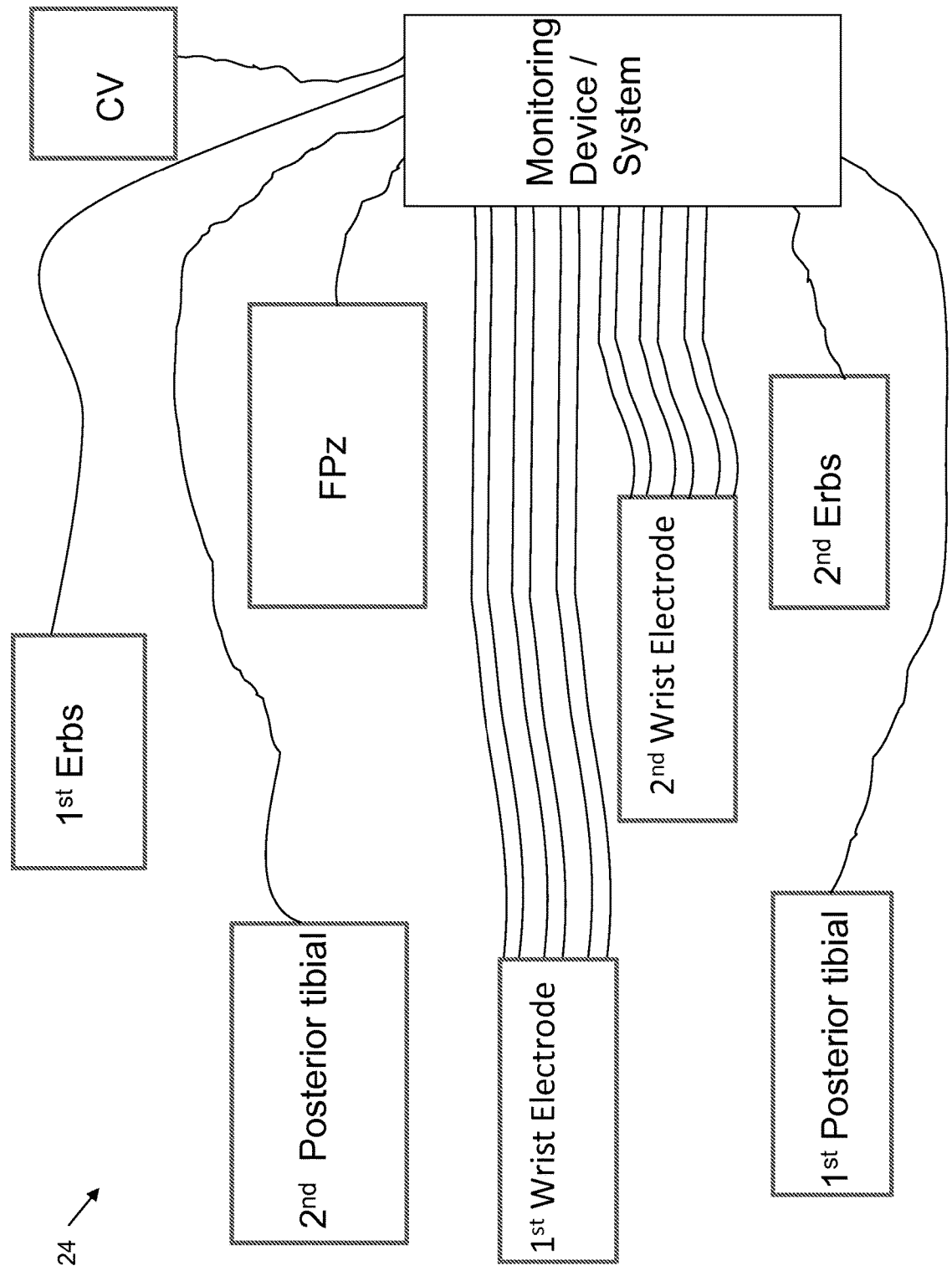
FIG. 2 is a schematic diagram of an electrode array that includes stimulation electrodes and baseline or reference electrodes according to an illustrative embodiment of the invention.

System, methods, and devices can use widespread peripheral/dermatomal evoked potential recordings. They can detect upper extremity neural dysfunction by stimulating and monitoring traffic through the branches of the brachial plexus. Since this traffic can be the variable and difficult to predict, the electrode array described herein is configured to increase the predictability by being selective and considering a set of three or more nerves as part of the stimulation and monitoring. An exemplary electrode array 24 is shown in FIG. 2 and can include various stimulating and recording electrodes as described herein. In one embodiment, the stimulating electrodes can be configured as part of a wristband configuration or as a wrist electrode as shown in FIG. 3.

Figure 3:
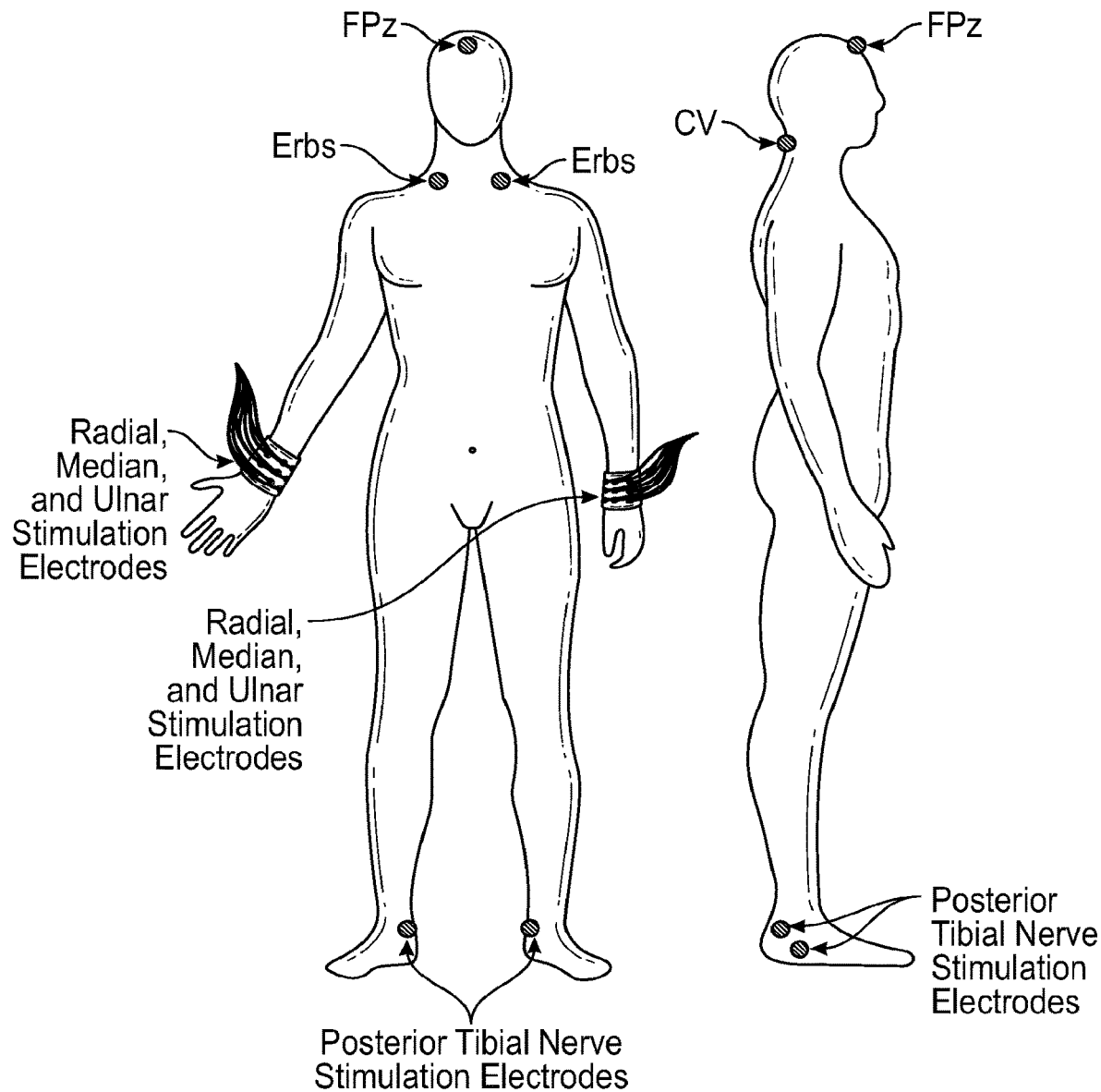
FIG. 3 is a schematic diagram of another electrode array shown relative to a patient according to an illustrative embodiment of the invention.

In FIG. 3, various stimulating and record electrodes are disposed on the skin of a patient. These electrodes can be used to monitor for various events of interest as detected by changes in responsive signals following electrode stimulation. The nerve signal changes when electrical stimulation is delivered at the wrist nerves and/or at the posterior tibial nerves. The recording electrodes capture and relay such changes as outputs for pre-processing and other processing steps by a given system embodiment such as that shown in FIG. 7. When a nerve is compressed or otherwise changed by a patient's position, such signals can be detected.

In one embodiment, use of all three nerves offers various advantages. Due to the anatomical variability and even the normal distribution of nerves in the brachial plexus it has been discovered that monitoring a single nerve for positional related nerve damage should include the monitoring of all the major nerves that pass through the wrist. While monitoring a single nerve (most commonly either the Ulnar nerve or the Median nerve) injuries can be missed. Monitoring only a single nerve results in a few patients awaking from anesthesia with some injuries. Monitoring all three nerves has resulted in no permanent injuries during experimental trials. Thus, in part, the invention relates to the discovery that monitoring of these three nerves can result in a significant increase in patient safety by reducing or stopping positional injuries.

Figure 4:
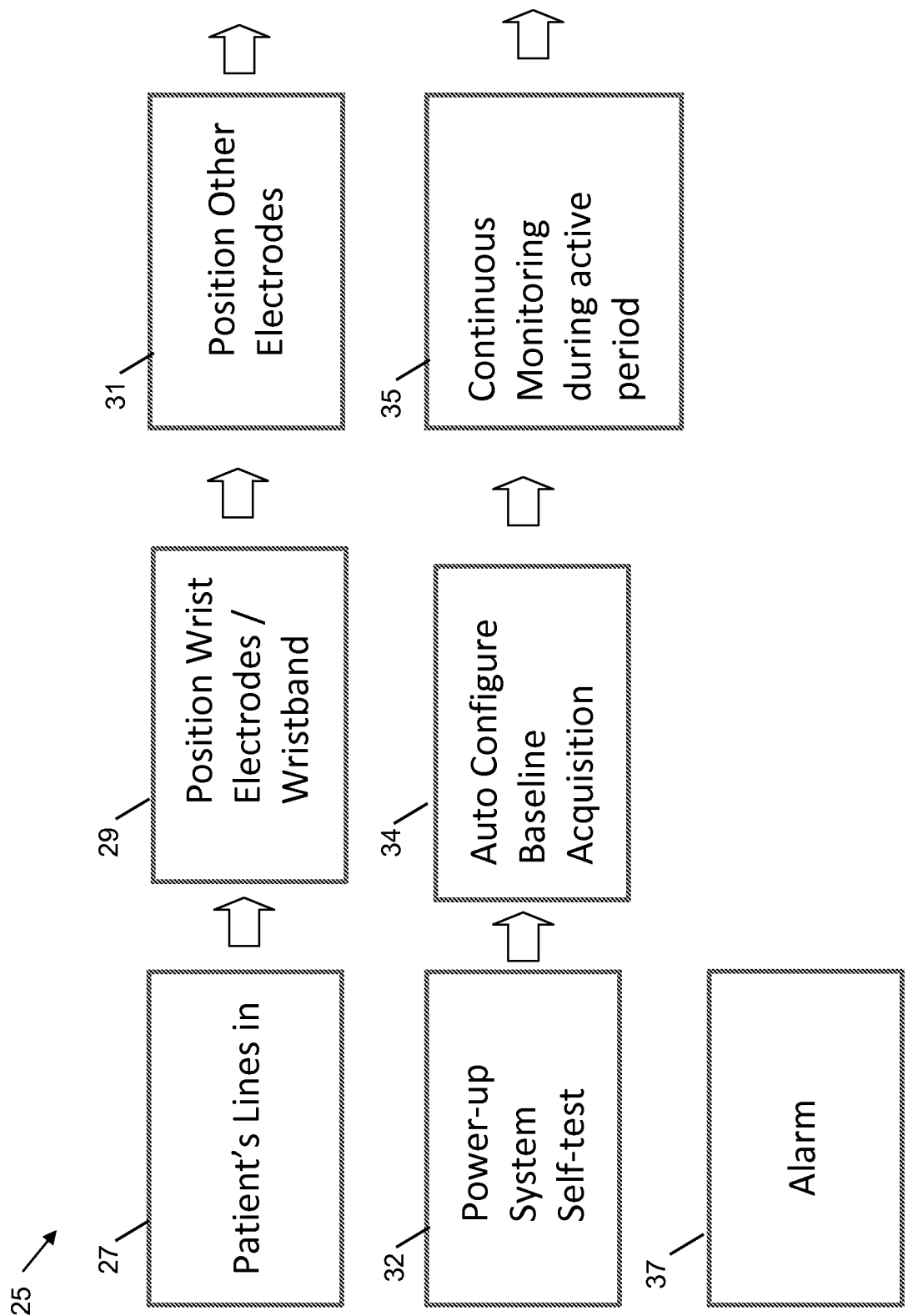
FIG. 4 is a series of stages or processing steps associated with configuring and collecting data associated with monitoring a patient during an active period according to an illustrative embodiment of the invention.

FIG. 4 describes a process flow 25 for a series of steps that can be performed to monitor a patient during an operation, experiment, clinical trial, or under other circumstances. Initially, the patient is medicated or receives anesthesia through lines (Step 27). Either before or after this step, stimulation electrodes such as a wrist electrode are positioned relative to the nerves to be stimulated (Step 29). The recording electrodes or other electrodes can then be positioned (Step 31). A system self-test can then be performed (Step 32). Data from the recording electrodes can be processed using a processor to perform an auto-configuration such that baseline nerve data can be acquired (Step 34). Continuous monitoring can be performed for an active period such as the operation time period or another time period (Step 23). If changes to the baseline signals deviate from one or more thresholds as determined by a processor or other device component an alarm is generated to indicate that a patient should be moved or that further operate involvement may be needed (Step 37).

In one embodiment, a wristband that is connected to one or more of the stimulation electrodes is used. Such a wristband can be used to stimulate a first and second or a first, second, and third nerve bundle as described herein. FIGS. 5A-6C show further details relating to using electrodes for nerve monitoring relative to a wrist.

Figure 5A:
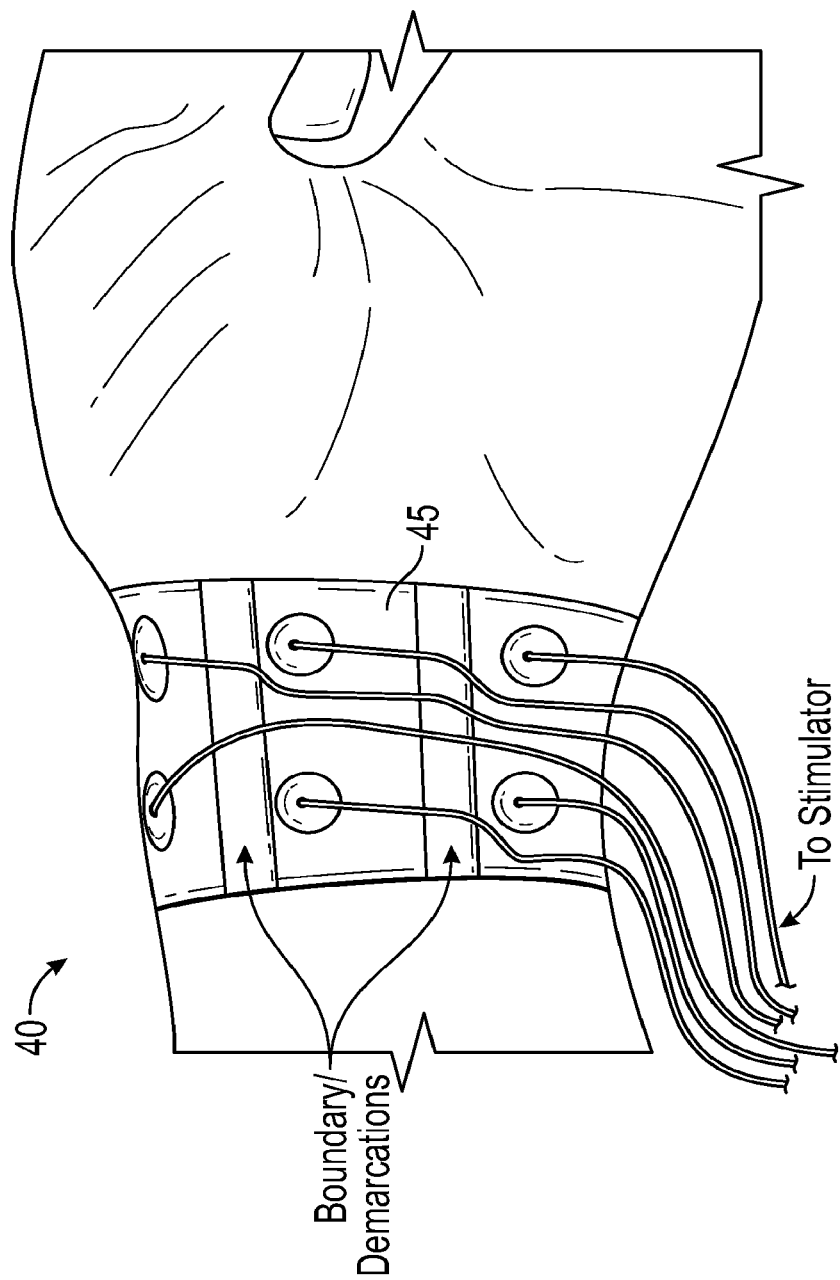
FIGS. 5A-5C are diagrams showing different electrode configurations suitable for applying to a wrist according to an illustrative embodiment of the invention.
Figure 5B:
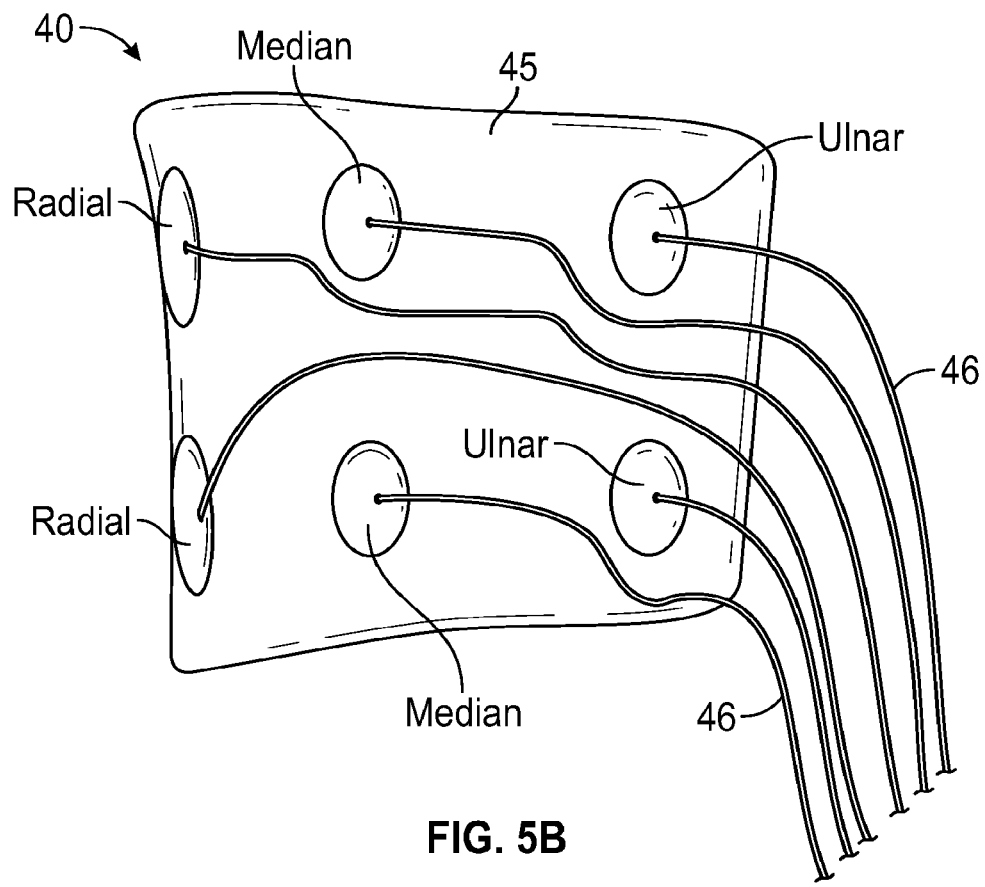
Figure 5C:
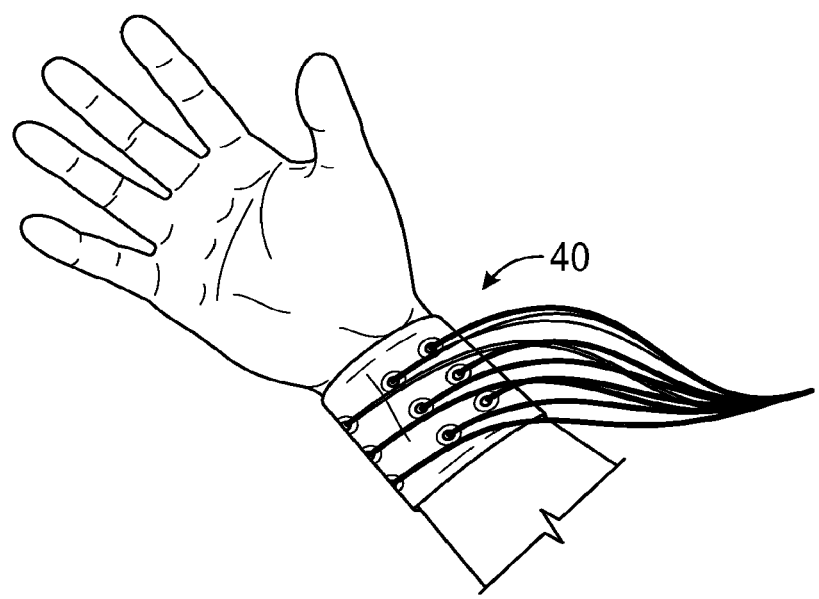

As shown in FIG. 5A-5C, the wristband 40 can include a flexible substrate 45 having an elongate or rectangular configuration. The substrate is sized and configured to cover some or all of the wrist and stably position stimulation electrodes relative to nerves in the wrist. The wristband 40 can be configured for quick placement on the wrist. In one embodiment, all three upper peripheral nerves are monitored (radial, ulnar and median) to avoid missing branches of the brachial plexus. In one embodiment, the nerves are monitored in and interleaved sequential fashion. In another embodiment, the nerves are monitored sequentially. One or more electrical leads 46 can be in electrical contact with a given electrode or anode/cathode pair. The electrodes can be gel electrodes in one embodiment. The systems described herein can monitor the lower extremity perineal nerve for lower extremity positioning neuropathies as shown in FIG. 3. Widespread transdermal stimulation and monitoring can detect and thus prevent more peripheral neural dysfunction missed by conventional SSEP monitoring. In one embodiment, widespread transdermal stimulation refers to activating or stimulating multiple nerves instead of just a single nerve.

FIGS. 5A and 5B shows the configuration of the electrodes placed on the wrist. Stimulation electrodes are placed in positions superficially peripheral nerves of interest. The wrist electrode can include six electrodes (anode and cathode for the three wrist nerves). A second set of electrodes that can be used as components of the electrode array include reference or recording electrodes. An exemplary representation of these recording electrodes is shown in the electrode array of FIG. 3 and FIG. 4. In one embodiment, the recording electrodes are also gel electrodes configured to stick to the patient's skin electrodes. They are sized and sufficiently flexible to be positioned at the bilateral Erb's points, FPz (frontal pole at midline) and CV. These electrodes, along with the stimulation electrodes, are shown in FIG. 3.

Needleless cortex monitoring is one advantage of the electrode array of FIG. 3. In one embodiment, the recording electrodes are configured to contact the skin to record nerve signals without piercing the skin. Thus, these electrodes are needleless in one embodiment. These types of electrodes are safer and result in a more user friendly experience. They also increase the likelihood that the system will be used by avoiding needle placement.

In one embodiment, all the wrist electrodes are contained in a single gel pack which can constitute a substrate. The substrate can be separated, stretched and modified as needed to allow for any configuration of the arterial line or wrist anatomy. Electrode positions in the wrist electrode are designed to improve operator use and prevent failing to monitor all three nerves. In one embodiment, the substrate forming the wristband that has anodes or cathodes disposed thereon can stretch and flex so that electrode position can be adjusted. In another embodiment, the anode and/or other the cathode portions of each electrode can be removed and repositioned relative to the substrate. In the case of some electrodes one or more substrate can be used such as a backing substrate and a gel substrate disposed thereon. The electrodes and substrate are sterile in one embodiment.

The wrist electrode is a multi-component device configured to provide low noise signals generated in response to evoked potentials to a monitoring system. All six electrodes can be applied at one time and can be used to secure any monitoring line for anesthesia (also referred to as an A-line) in place. Thus, the wrist electrode can be used to secure other electrodes while monitoring the wrist nerves. One issue with standard electrode placement is the securing tape used with one or more A-lines gets in the way. In order to address that problem the wrist electrode can be made of a flexible transparent dressing material such as Tegaderm. The anode and cathode for each electrode pair can be disposed on such a substrate 45 with the leads 46 flowing outwards to a monitoring device. The electrode kit that includes a wrist electrode can include Mastisol® to help secure the electrode or components thereof.

In one embodiment, an operator places three sets of electrodes over each of the main nerves at the wrist (the Ulnar, Median, and the Radial) for stimulation. This requires knowledge of the anatomy. It is also time intensive to place the six electrodes (anode and cathode for each stimulation pair). In order to improve the efficacy and the accuracy of placement for the untrained user, a single device where each pair is encased or disposed in a band is used as shown in FIG. 5B. The band is made of a comfortable material with embedded gel electrodes. Six electrodes are used in one embodiment (three anodes and three cathodes). In one embodiment, there are three marks on the band to help in proper anatomic placement. The first mark is in the center of the band and will line up with the center of wrist. There are two lateral marks that will, when properly placed lie over the ulna and radius bones.

Material between the center pair of electrodes and the two lateral electrodes can be adhesive-free. Thus, that area to forms a fold for a smaller wrist. Adhesive is placed at the lateral segments of the band, under the electrodes and in the middle of the band to help hold the band in place in one embodiment. The segments with no adhesive allow for band position modifications due to A-line placements.

In one embodiment, the wristband will have two removable protective covers disposed over the adhesive. Removal of the first protective cover will expose a light abrasive pad with alcohol. This is rubbed over the wrist to improve the contact between the electrodes and the wrist. In turn, this reduces the contact resistance and improving the delivered stimulation signal. After cleaning, the wrist this pad is removed exposing the adhesive and electrodes. Due to the variation in A-line placement techniques some modification of the A-line securing tape and/or placement of the stimulation leads may be needed in some embodiments.

FIGS. 6A-6C show various cross-sections of a wrist electrode with anode/cathode pairs for each of Radial nerve R1/R2, Median nerve M1/M2, and Ulnar nerve U1/U2. Each anode is a type of electrode in one embodiment. Each cathode is a type of electrode in one embodiment. The substrate 45 can be fabricated from a mesh, a tape, multiple substrates, gels, and other materials. Elements A1 and A2 can be disposed in or one substrate 45 and provide a demarcation or boundary to guide any end user. The elements A1, A2 can be tape, pigments, dyes or other materials. Other lines or boundaries can be disposed in or on the substrate to facilitate proper placement. The only element that needs to contact the skin is the surface of each electrode. As a result, the wristband need not adhere to the skin at every region along its skin contacting side. Accordingly, in one embodiment the space between each electrode can be adjusted by folding for different wrist sizes.

Figure 7:
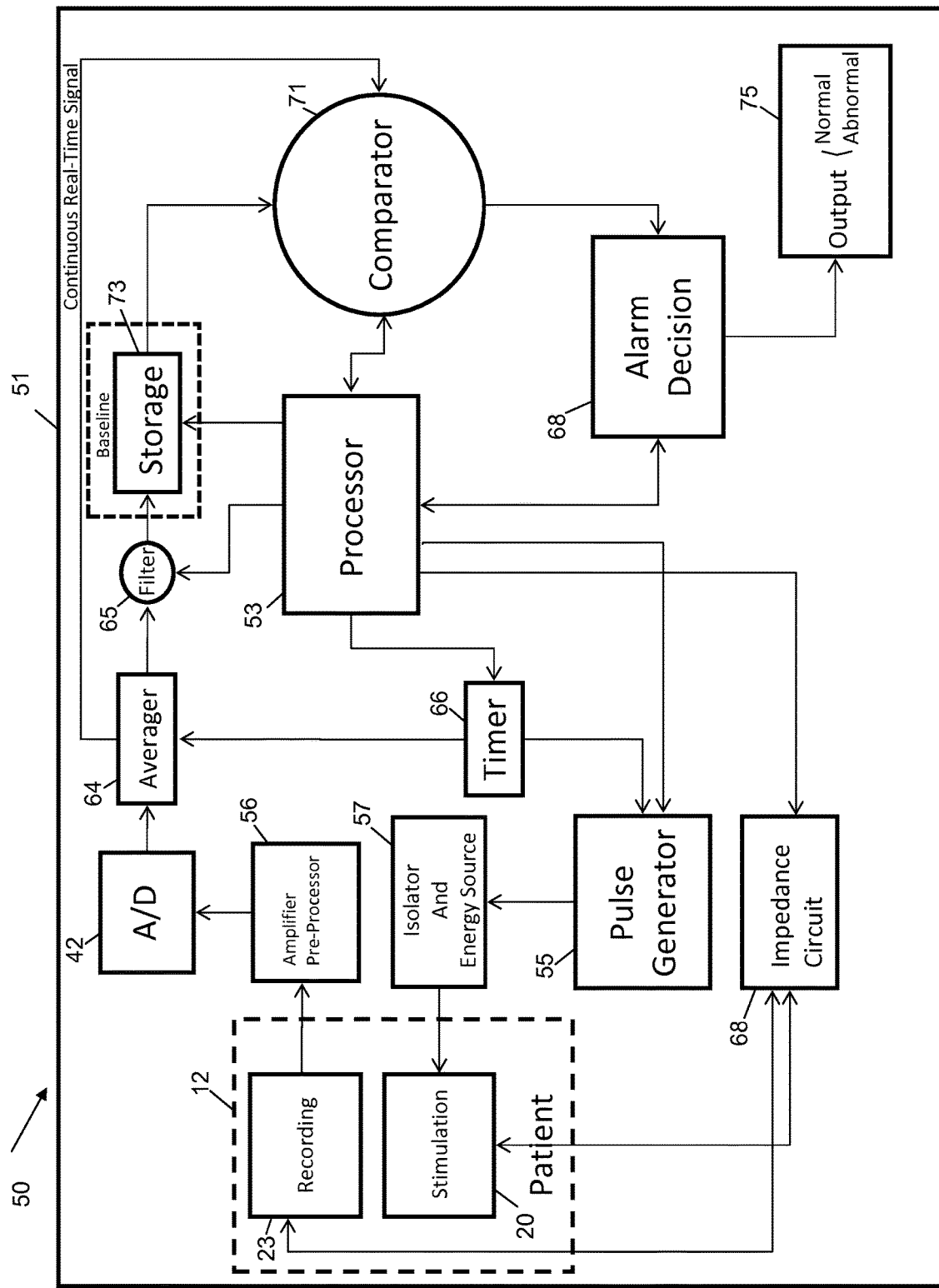
FIG. 7 is a schematic diagram of a monitoring system according to an illustrative embodiment of the invention.

FIG. 7 illustrates an example monitoring system 50 including a processor 53 and various other components. An exemplary housing 51 is shown. The input/output interface can include a pulse generator 55 and one or pre-amplifiers 56. These can be isolated from other system components using an isolator or other devices 57. The pulse generator 55 can include a power source connected to the isolator. In one embodiment, the pulse generator energy source is optically isolated from the main processor and pulse generating circuit. These can be separate elements in one embodiment of the monitoring system. Each pre-amplifier is in electrical communication with an electrode or lead or cable connected thereto. This arrangement minimizes or reduces external noise.

The pulse generator 55 can either be disposed inside the housing of the monitoring device or at the electrode connectors. The pulse generator 55 defines properties of the pulses and generates the actual pulse based on the timing circuit 66. The processor 53 defines the pulses by defining the amplitude and pulse width of the pulse.

Once the pulse is initiated at the pulse generator, it passes through the isolation and energy source circuit 57 for delivery to the patient through stimulation electrodes. This circuit isolates the patient from the major AC line signal in order to protect the patient from any grounding or line failures. It also contains protection circuitry to protect the stimulator from stray spikes from cautery or external defibrillators. At specified time intervals, the processor halts the collecting of data for a specified time. During this halt state it checks the impedance of each electrode. This is to assure that the system is properly working. This circuit can also be initiated if the system starts to detect excessive noise or other artifacts. When the system detects frequencies in the band of the cautery devices the processor will not initiate this circuit. Recording is performed by circuitry at units close to the electrodes on the patient and digitized at those areas. This configuration minimizes or reduces noise entering the system.

The processor 53 performs various actions and steps in the system 50. It generates the timing for the stimulation signal to each nerve by controlling timer 66. The pulses to control both the data acquisition and the averaging system also referred to as the averager 64 are generated by the processor 53. The programming of the alarm criteria can be performed using instructions that execute on the processor 53. The comparison algorithm and the error checking can also be performed by the processor.

In one embodiment, the processor contains or is in electrical communication with a digital signal processor for signal processing. The timer 66, after receiving the appropriate signals from the processor 53, controls the sequence of stimulation (i.e. when each stimulator will fire) a control signal imitates the start of the specific average for the recording of that electrical or evoked potential.

In one embodiment, each nerve is checked in a sequential fashion. The timing circuit or timer 66 controls that sequence and also the appropriate averaging sequence at the instruction of the processor 53. After the initial baseline signals are acquired and stored, the processor 53 executes a running average algorithm, or multiple averaged algorithm (depending upon the user configuration or internal determination of the noise level in the system) to compare the input signals to the stored baseline. The baseline signal can be stored in a memory storage device 73. This continues over a time period T in one embodiment. T can correspond to a perioperative time period in one embodiment.

If the comparator 71 determines a significant discrepancy between the baseline and the real-time signal, then an alarm decision 68 is made. This can be subject to a determination that the noise level is considered acceptable. This can reduce false triggering and alarming. Various filters 65 and other components can be used to reduce signal noise. Once an alarm state is generated in response to a threshold or other parameter being detected, an alarm signal is sent to an output 70. The output can be a display, an indicator, such as an LED, or a speaker.

In one embodiment, a subsequent step in the process includes transmitting the digital signal to an averager 64 as shown in FIG. 7. A continuous moving average is used by the system 50 in some embodiments. Software is used in conjunction with the processor to determine suitable or optimal averaging weights based on room noise and signal quality. This is defined for each signal received from an electrode and controlled by the processor 53. Filtering of the signal removes unwanted elements of the signal, such as EKG artifact, if needed based on a noise threshold. Enhancing low SNR signals using specific signal techniques (i.e. wavelets) to extract the signal in the least amount of averaging can also be performed.

Prior to continuous averaging, a baseline signal is obtained for comparison. The baseline signal is recorded at the start of an operation, but can also be initiated at any time by the end user. A new baseline can be selected in response to modifications in the anesthesia technique or type, electrode changes, modifications in the external signal artifices and based on other factors.

Each nerve's baseline is stored independently such as in memory storage 73. This baseline signal is used as one input to the comparator 71. Once the baseline signal is stored, the output of the moving average is compared relative to the baseline at various time periods. The comparator thresholds and morphology parameters are controlled by the processor 53. If a change that has occurred on the waveform passes any of these thresholds the comparator 71 sends a signal to the processor and to the alarm decision unit. Depending upon the state of the system 50, as defined by the processor, the alarm decision unit or module 68 generates an alarm. Also, if the processor 53 detects any abnormalities in the system's operation an alarm signal is sent to the end user visually, audibly, both or otherwise.

After a self-test power-up routine, there is an auto-configure process that calibrates and setup the system. In one embodiment, a calibration routine can be performed to test the operation of the wrist electrode before starting an operation. The auto configure process can include testing impedances and indicating if there are any problems. If the system passes, it will acquire baseline data from the reference or recording electrodes. A single baseline is acquired for each stimulation set. A quality number can be assigned based on the SNR. The SNR is measured between the baseline noise level taken between 35 and about 50 mSec for the upper SSEP and about 10 to about 25 mSec for the lower SSEP and the signal for the primary N20 to baseline and the P22 to baseline. This SNR is determined for different averaging counts. The system auto-sets itself for an SNR greater than at least about 10 dB. Active noise filtering can also be used to reduce unwanted noise. After performing this initial set-up, a plurality of average sets, such as between about 3 and about 10 sets, is performed for reliability and reproducibility. These are stored and used later for comparisons of changes in evoked potentials over time.

A warning threshold is adjustable by the user, but a default setting is provided in one embodiment. The alarm criteria for SSEP's can be set as a reduction in signal amplitude of about 50% and a latency shift of about 10% relative to a baseline set. In order to generate a warning during an operation, the threshold can be set at an intermediate value relative to the alarm criteria to get a warning that something may be happening prior to this event. If the system 50 is part of the anesthesia machine, it can use data from that machine's standard monitor to help rule out anesthesia and vital effects. The processor can use this data feed and execute software designed to identify other effects based on the anesthesia machine data. If the default signal amplitude is about 40% then if that level is reached the monitoring system will check for possible changes in other channels and changes in the a anesthesia and vitals and generate a warning or another indication of a potential problem.

The processor may be any suitable processing device or set of processing devices, such as a microprocessor, a microcontroller-based platform, a computer-processor such as an Intel or AMD processor, a suitable integrated circuit, or one or more application-specific integrated circuits (ASICs).

As generally noted above, a processor of the monitoring system is configured to communicate with, configured to access, and configured to exchange signals with a memory device or data storage device or an adapter. In one embodiment, the adapter is configured to cause nerve signals and associated alarms to be displayed on an anesthesia machine or collect data there from. In various embodiments, the memory device of the monitoring system includes random access memory (RAM), a hard drive, and other forms. In other embodiments, a memory device includes read only memory (ROM). In certain embodiments, a memory device of the monitoring system includes flash memory and/or EEPROM (electrically erasable programmable read only memory). It should be appreciated that any other suitable magnetic, optical, and/or semiconductor memory may operate in conjunction with the monitoring system disclosed herein.

In certain embodiments, as generally described above, a memory device of the monitoring system stores program code and instructions executable by a processor of the monitoring system to control the monitoring system, generate threshold, and process data feeds. A memory device of the monitoring system also stores other operating data, such signal traces, electrode properties, relative electrode placement, alarm triggering routines, impedance information and/or applicable nerve stimulation and baseline tracking rules. In various embodiments, part or all of the program code and/or the operating data described above is stored in one or more detachable or removable memory device including, but not limited to, a cartridge, a disk, a CD ROM, a DVD, a USB memory device, or any other suitable non-transitory computer readable medium.

The exemplary monitoring system illustrated in FIG. 7 includes one or more output devices. One or more output devices of the monitoring system are one or more display devices configured to display any alert, signal trace, or stimulation signal detected or generated by the monitoring system and any suitable information associated with a given monitoring period such as perioperative period. In certain embodiments, the display devices are connected to or mounted on a housing of the monitoring system. In various embodiments, the display device serves as multiple source of time varying patient information.

In various embodiments, the display devices include, without limitation: a monitor, a television display, a liquid crystal display (LCD), a display based on light emitting diodes (LEDs), or any other suitable electronic device or display mechanism. In certain embodiments, as described above, the display device includes a touch-screen with an associated touch-screen controller. It should be appreciated that the display devices may be of any suitable sizes, shapes, and configurations amenable for displaying patient data.

The display devices of the monitoring system are configured to display one or more alarms, signal tracings, or other patient derived data. In certain embodiments, one output device of the monitoring system is a sound generating device. The monitoring system illustrated in FIG. 7 can include one or more speakers to generate an indication of an alarm or that a patient needs to be moved to ameliorate the neuropathy.

In one embodiment, the system of FIG. 7 can either be part of an anesthesia machine or a stand-alone monitoring system. Each SSEP can be displayed for user evaluation, yet the main interface is a color coded or symbol coded output. These outputs can be configured to indicate a normal system and signal, an abnormal signal, or a system error that includes.

Figure 8:
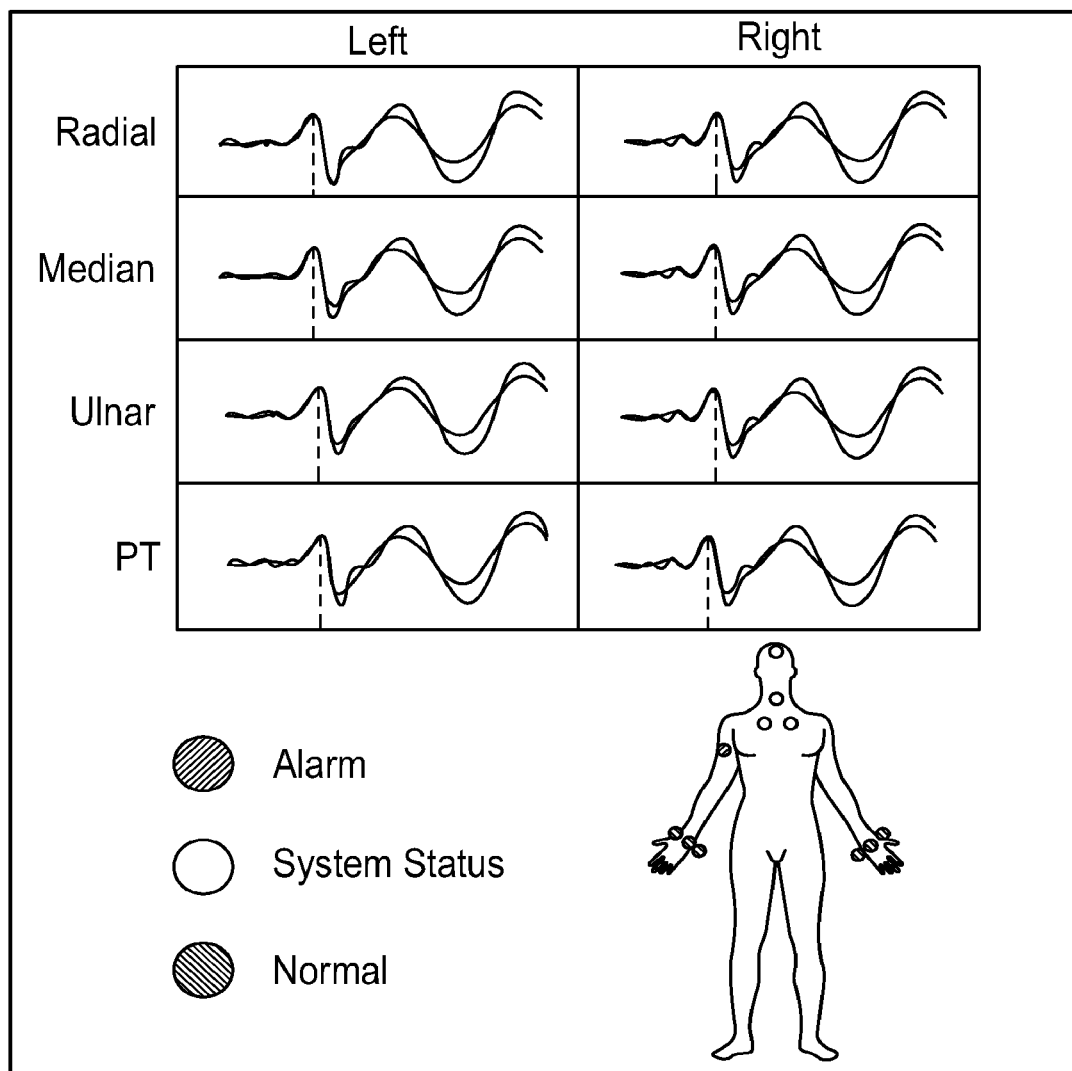
FIG. 8 is a user interface screen showing evoked potential signals varying over time and various indicators suitable for evidencing an alarm, system status, or normal state according to an illustrative embodiment of the invention.

There are one or more indicators configured to display system information. Three can be used as shown in FIG. 8 in one embodiment. One or more indicators can be configured to indicate that (1) All electrode impedances good or bad (stimulation, recording, and ground) and an indication of which is bad (red) or good (green); (2) System status (Booting up (yellow flashing), operational (green), impedance testing (blue), initial baseline (flashing green), system error (red)); and (3) all normal light (green when no issues— red when there is an issue). For a stand-alone monitoring unit, each electrical or evoked potential waveform is displayed with its baseline. For the anesthesia based-system, any waveform can be displayed by choosing a configuration window. The percentage change from a baseline of each evoked potential wave peak or amplitude value can be shown using various indicators. Various other indicators and graphical interfaces can be used. In one embodiment, the point in which the amplitude decreases by about 50% and/or the latency increases by 10% is when an alarm is triggered. A bridge to the temperature sensor to define the proper latency change can be used since temperature is a normal reason for latency to change. This can improve the accuracy of alarm triggers.

Figure 9:
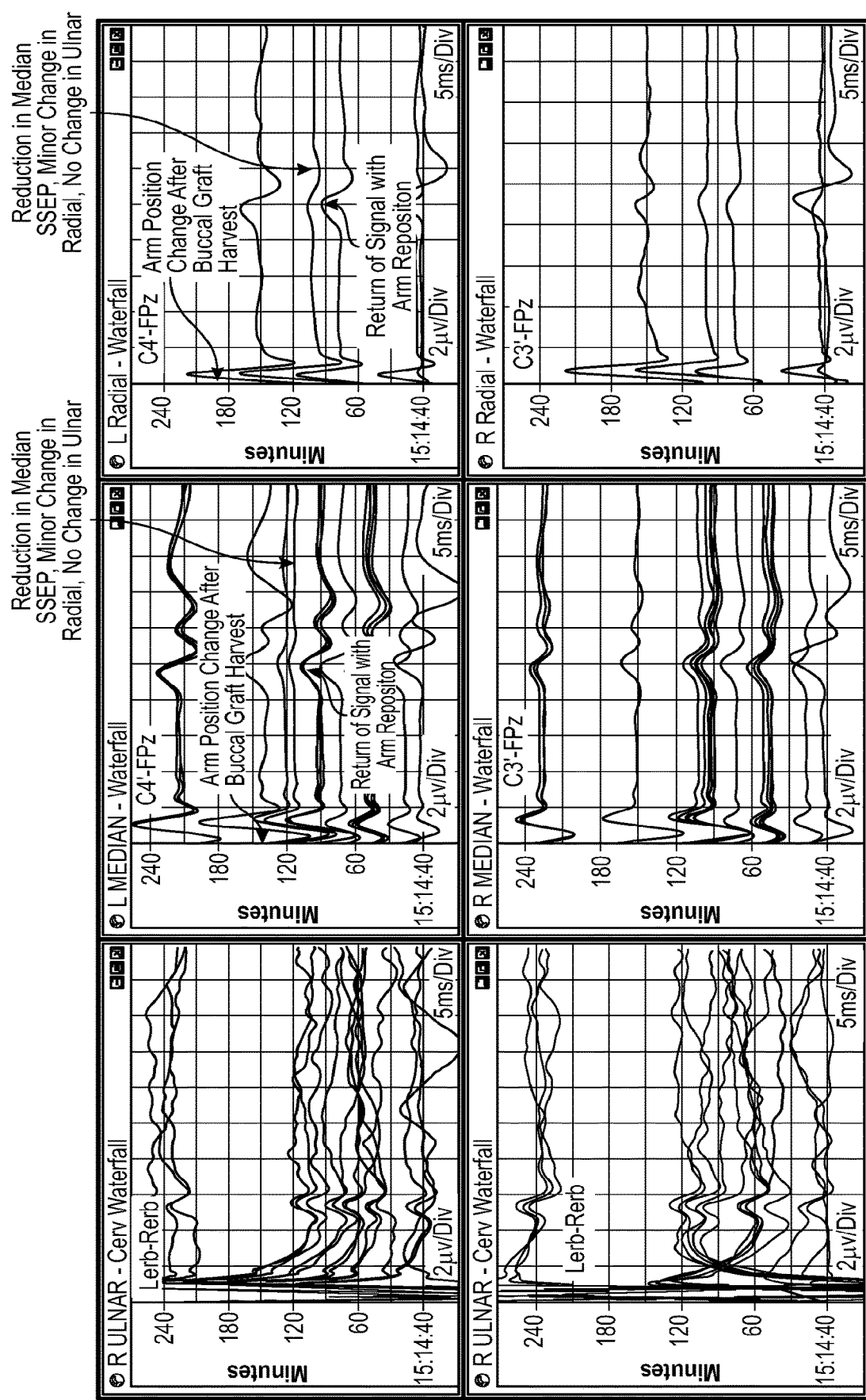
FIG. 9 is a series of plots showing time varying evoked potential signals associated with one or more nerves according to an illustrative embodiment of the invention.
Figure 10A:
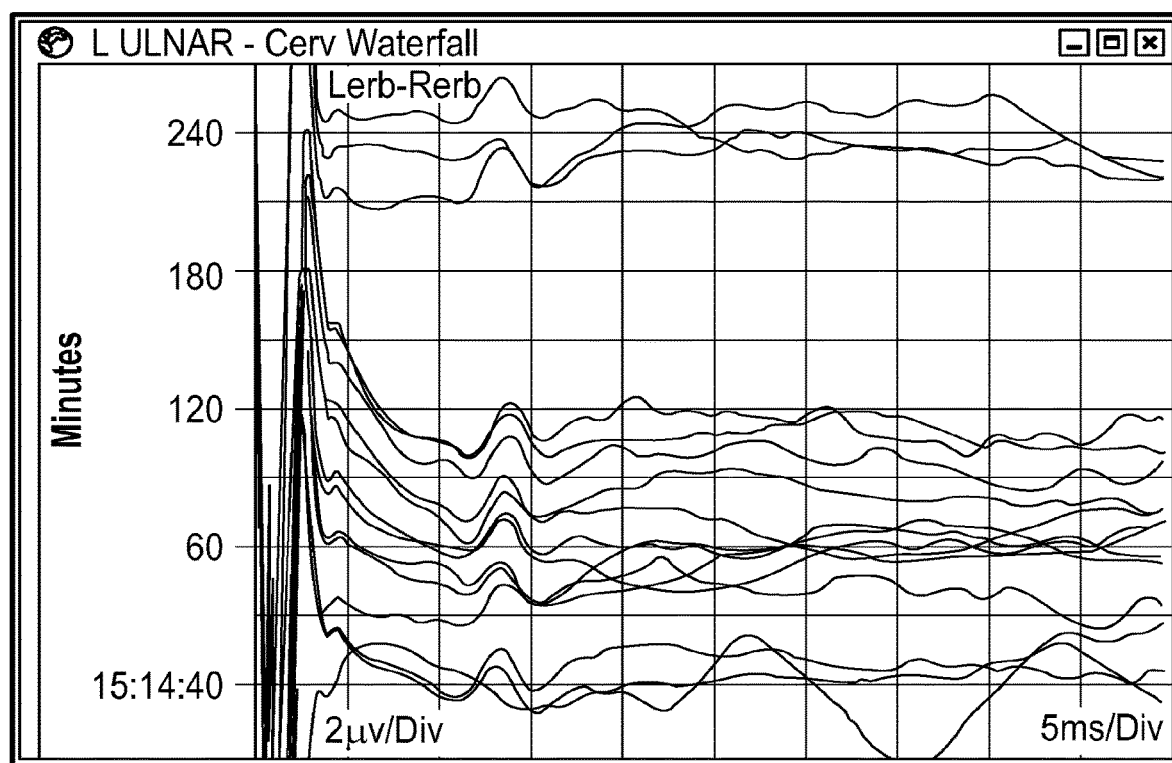
FIGS. 10A-10F show individual views of the signal plots shown in FIG. 9 according to an illustrative embodiment of the invention.
Figure 10B:
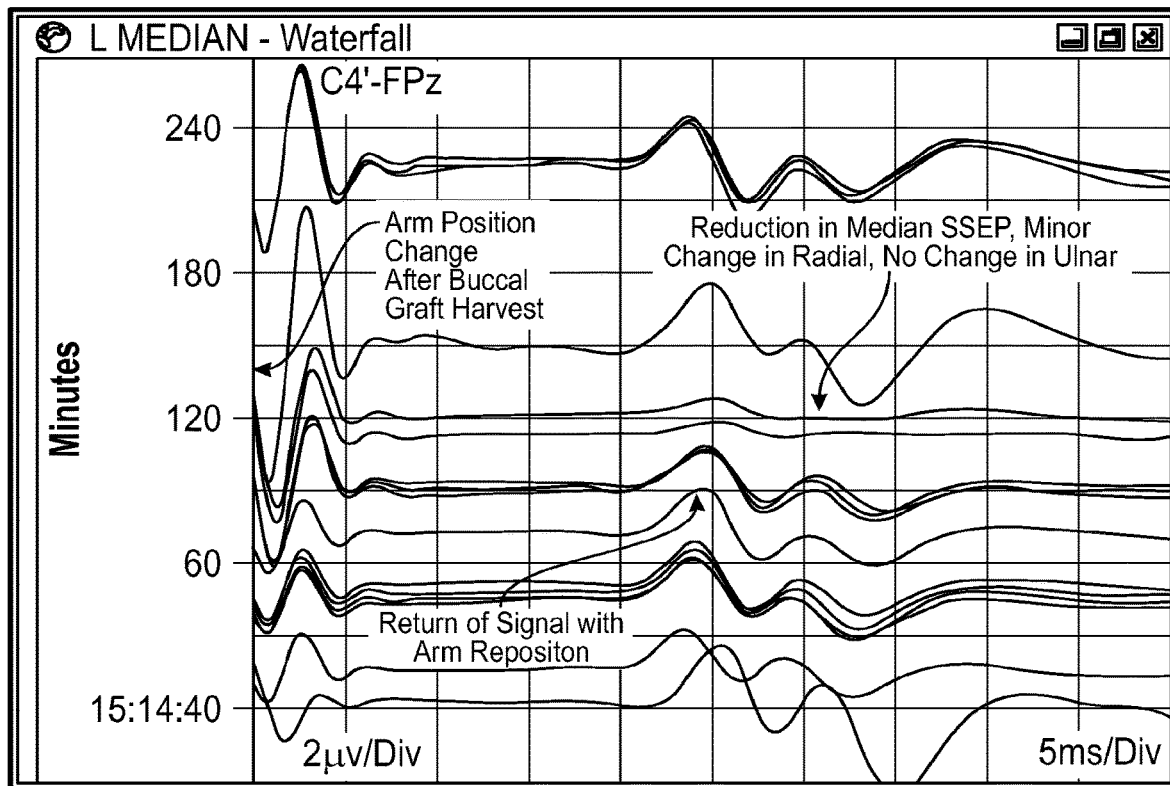
Figure 10C:
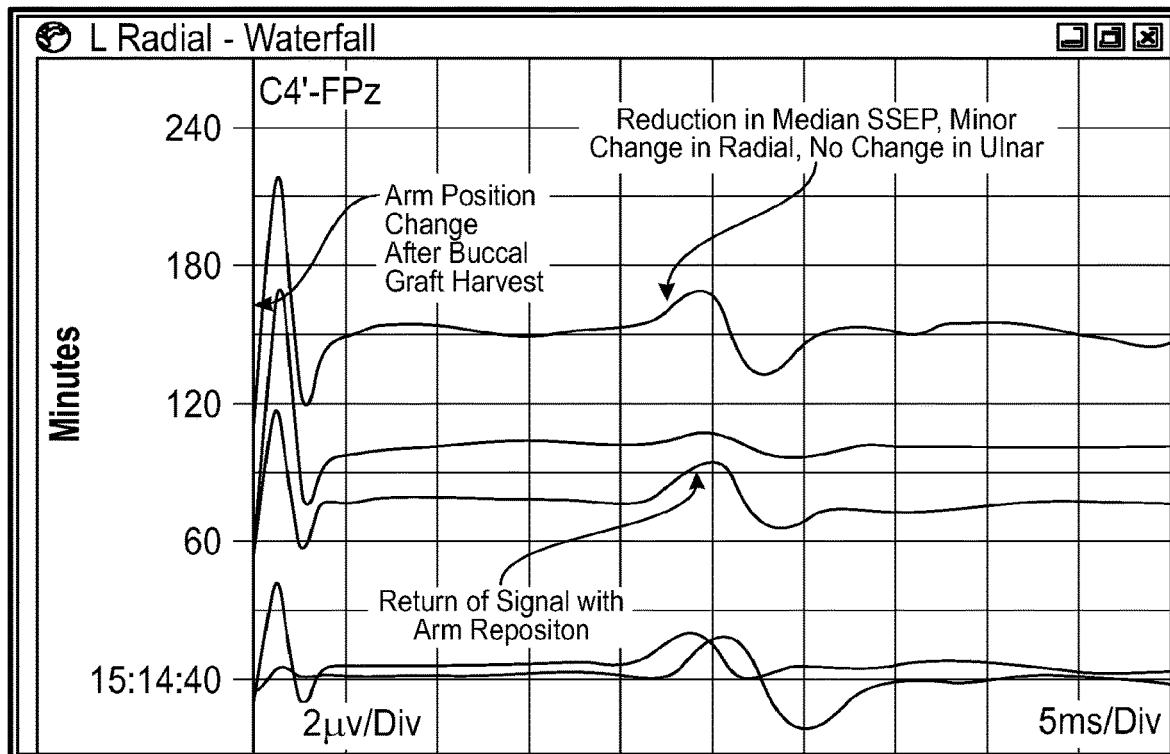
Figure 10D:
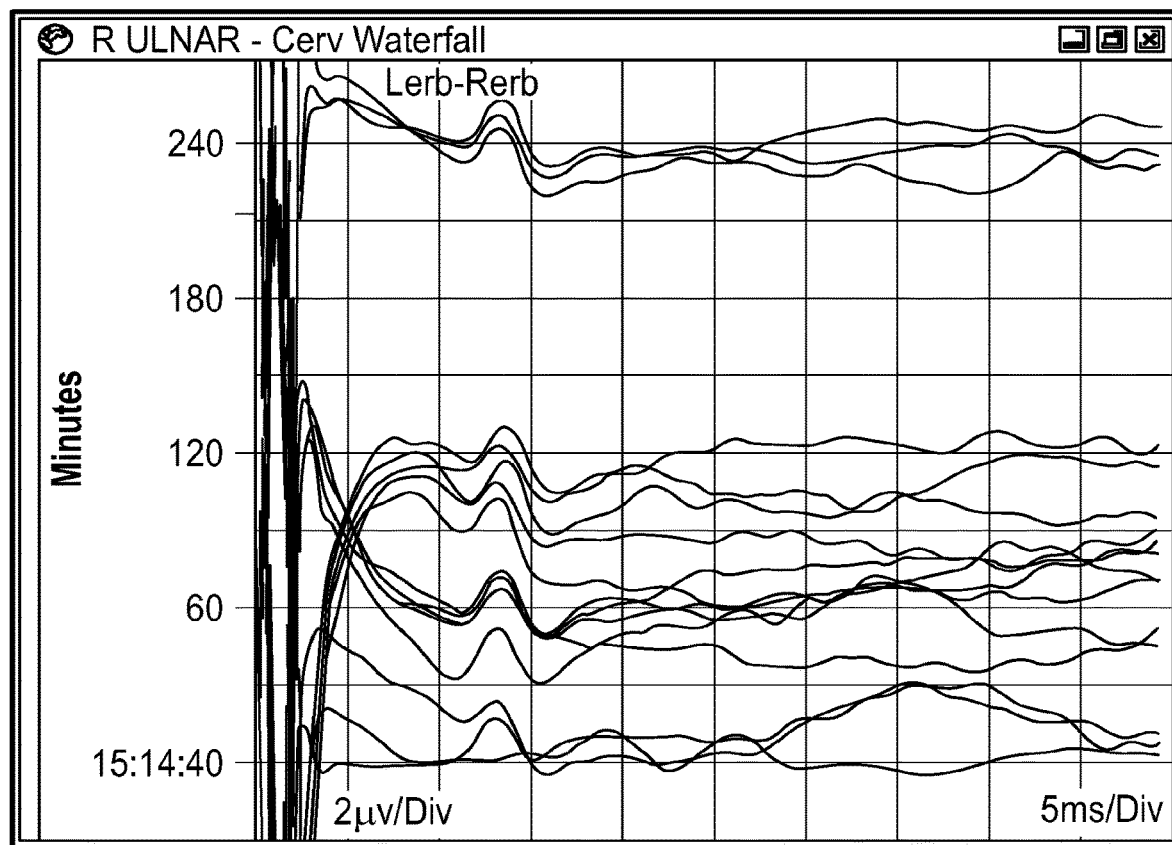
Figure 10E:
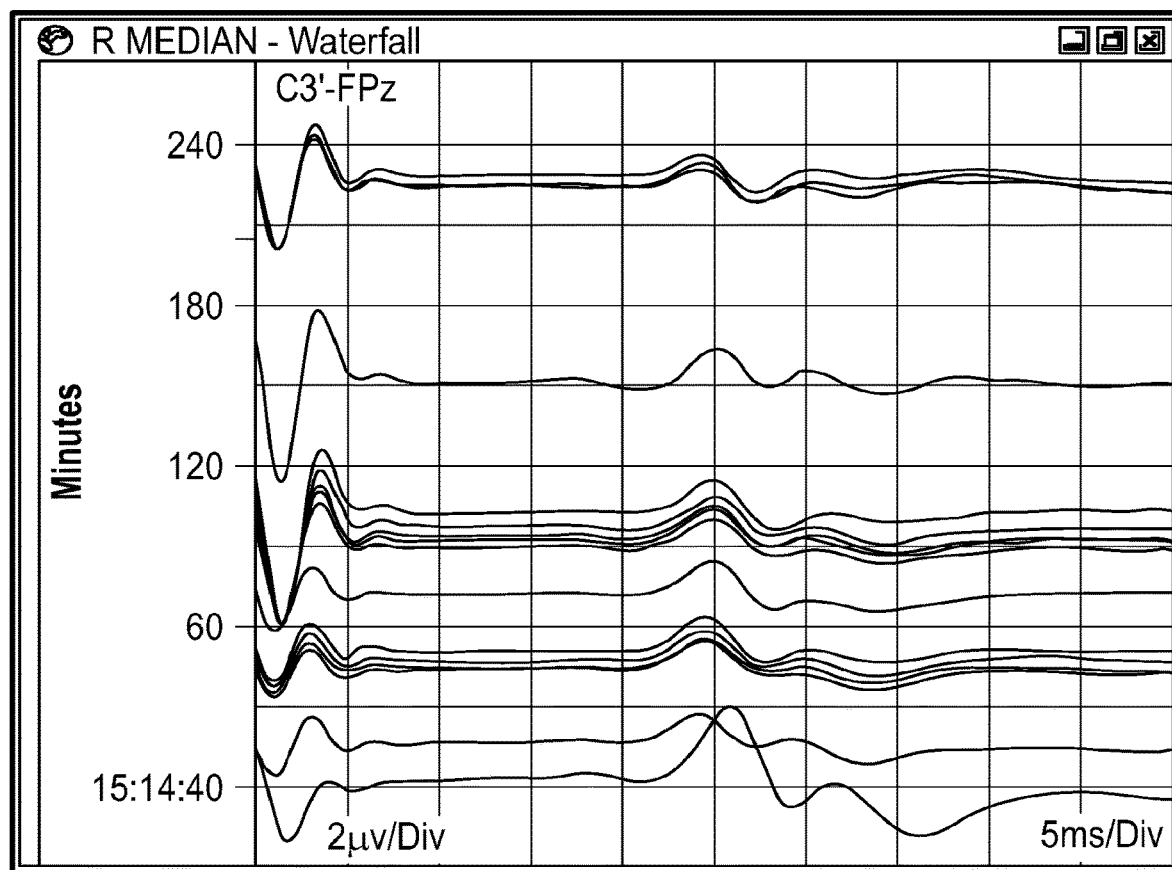
Figure 10F:
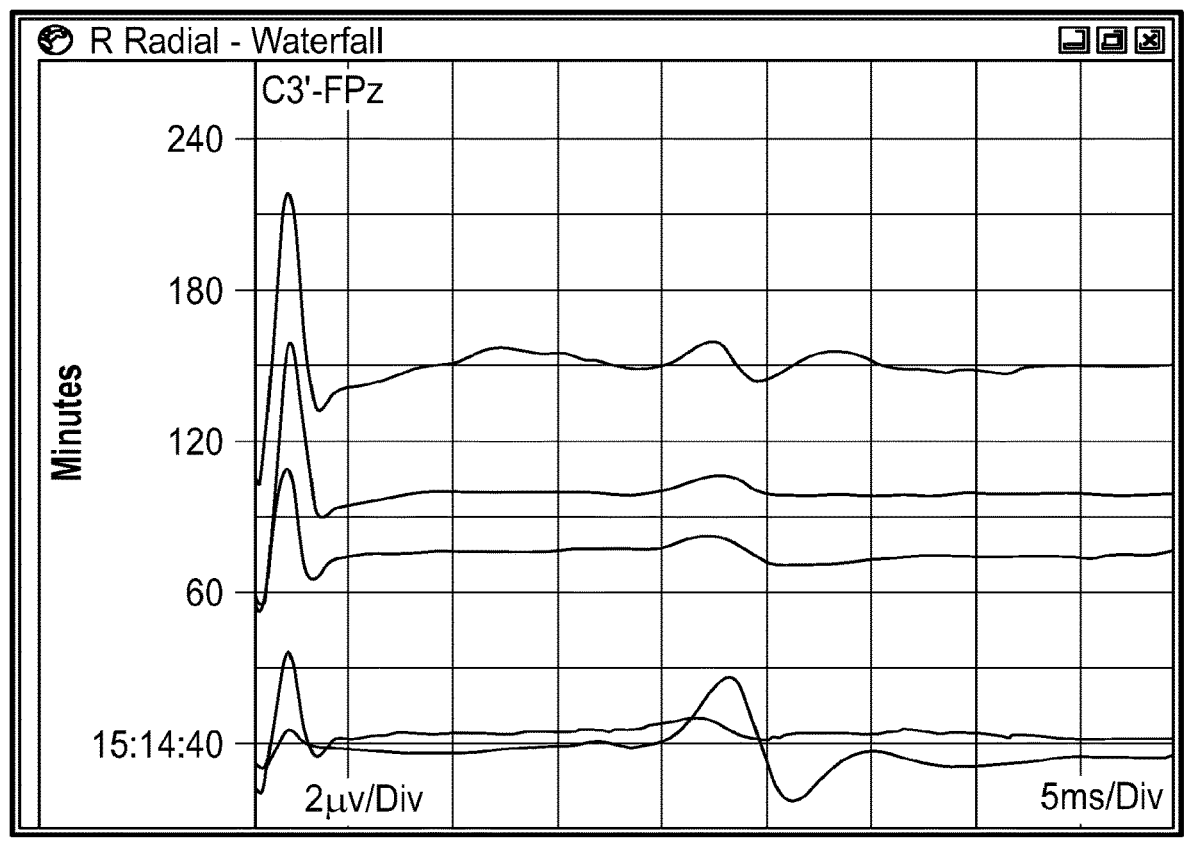

An example of changed signal is shown in FIG. 9 and more particularly in FIGS. 10B and 10C. These figures show a user interface screenshot displayed in an embodiment suitable for use in the operating room. The top panels are from stimulation at the left wrist and the bottom panels are from stimulation at the right wrist in FIG. 9. The left to right sequence of panels show the responses from stimulation of the following nerves: Ulnar, Median, and Radial in FIG. 9. The arrows indicate significant changes when stimulating both the medial and radial nerve on the left wrist. They also show no change occurring when stimulating the ulnar nerve and no change when stimulating the right side. This exemplary data set was obtained using the electrode array configuration of FIGS. 2 and 3.

Non-Limiting Software Features and Embodiments for Implementing SSEP Monitoring Methods and Systems The following description is intended to provide an overview of device hardware and other operating components suitable for performing the methods of the invention described herein. This description is not intended to limit the applicable environments or the scope of the invention. Similarly, the hardware and other operating components may be suitable as part of the apparatuses described above. The invention can be practiced with other system configurations, including personal computers, multiprocessor systems, microprocessor-based or programmable electronic device, network PCs, minicomputers, mainframe computers, and the like.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as averaging, thresholding, determining, generating, alarming or the like, refer to the action and processes of a computer system, processor, circuit or similar electronic device, that manipulates and transforms data represented as physical (electronic) quantities within electronic registers and memories into other data similarly represented as physical quantities within the computer system memories or registers or other such information storage, transmission or display devices.

The present invention, in some embodiments, also relates to apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the invention may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using the electrodes and received by the system is implemented as a set of computer program instructions that is converted into a computer executable form, stored as such in a computer readable medium, and executed by a microprocessor under the control of an operating system. Thus, evoke potential signals captured by reference electrodes are transformed into processor understandable instructions suitable for generating alarms and nerve signal data and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as baseline nerve signals, average sets, amplitude percentage changes, latency values, stimulation signals, post-stimulation nerve signals, electrode array configuration information, neuropathy types, alert thresholds, predetermined deviation limits, and other data.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

The aspects, embodiments, features, and examples of the invention are to be considered illustrative in all respects and are not intended to limit the invention, the scope of which is defined only by the claims. Other embodiments, modifications, and usages are apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

It should be appreciated that various aspects of the claimed invention are directed to subsets and substeps of the techniques disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Accordingly, what is desired to be secured by Letters Patent is the invention as defined and differentiated in the following claims, including all equivalents.

What is claimed is:

1. An electrode array configured to generate and monitored evoked potentials comprising:
    a first pair of electrodes,
    a second pair of electrodes,
    a third pair of electrodes, and
    an elongate first flexible substrate, the first electrode pair, second electrode pair, and third electrode pair disposed in or on the first substrate, wherein said first electrode pair, second electrode pair, and third electrode pair are configured on said first flexible substrate such that when said electrode array is placed on or over a wrist of a patient said first electrode pair is disposed over a radial nerve in the wrist, said second electrode pair is disposed over a median nerve in the wrist, and said third electrode pair is disposed over a ulnar nerve in the wrist, and wherein the flexible substrate has one or more demarcations configured to identify a boundary between one or more nerves or bones disposed relative to nerves to assist in proper anatomic placement of said electrode array on or over said wrist of a patient such that said first electrode pair is disposed over said radial nerve in the wrist, said second electrode pair is disposed over said median nerve in the wrist, and said third electrode pair is disposed over said ulnar nerve in the wrist.

2. The electrode array of claim 1, further comprising a first electrical lead having an electrode contacting end and a monitoring device contacting end, the electrode contacting end in electrical communication with at least one electrode in the first pair of electrodes, a second electrical lead having an electrode contacting end and a monitoring device contacting end, the electrode contacting end in electrical communication with at least one electrode in the second pair of electrodes, a third electrical lead having an electrode contacting end and a monitoring device contacting end, the electrode contacting end in electrical communication with at least one electrode in the third pair of electrodes.

3. The electrode array of claim 1, wherein one electrode in each pair is an anode and the other electrode in each pair is a cathode, wherein all three anodes are arranged substantially in a first row and wherein all three cathodes are arranged substantially in a second row.

4. The electrode array of claim 1, wherein the electrode array comprises a second substrate disposed on the first substrate, and said first, second and third electrode pairs are disposed in or on the second substrate.

5. The electrode array of claim 4, wherein the second substrate is a gel.

6. The electrode array of claim 1, wherein said first electrode pair, second electrode pair, and third electrode pair are configured on said first flexible substrate such that when said electrode array is placed on or over a wrist of a patient each of said first electrode pair, said second electrode pair, and said third electrode pair are disposed on a ventral surface of the wrist.

* * * * *